(12) United States Patent
Uchida et al.

(10) Patent No.: US 9,820,646 B2
(45) Date of Patent: Nov. 21, 2017

(54) IMAGE PROCESSING APPARATUS, IMAGE PROCESSING METHOD, AND OPTICAL COHERENCE TOMOGRAPHY APPARATUS

(71) Applicant: CANON KABUSHIKI KAISHA, Tokyo (JP)

(72) Inventors: Hiroki Uchida, Tokyo (JP); Yukio Sakagawa, Tokyo (JP); Krzysztof Marek Piotrowski, Wroclaw (PL)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/206,114

(22) Filed: Jul. 8, 2016

(65) Prior Publication Data
US 2017/0014025 A1    Jan. 19, 2017

(30) Foreign Application Priority Data
Jul. 13, 2015 (JP) .................. 2015-140052

(51) Int. Cl.
| | |
|---|---|
| *A61B 3/14* | (2006.01) |
| *A61B 3/00* | (2006.01) |
| *A61B 3/10* | (2006.01) |
| *G06T 7/00* | (2017.01) |
| *A61B 3/12* | (2006.01) |

(52) U.S. Cl.
CPC .......... *A61B 3/102* (2013.01); *A61B 3/0025* (2013.01); *A61B 3/12* (2013.01); *G06T 7/0012* (2013.01)

(58) Field of Classification Search
USPC .................................... 351/200–246
See application file for complete search history.

(56) References Cited

U.S. PATENT DOCUMENTS

| | | | |
|---|---|---|---|
| 9,521,316 B2 * | 12/2016 | Eguchi | H04N 5/23229 |
| 2011/0141259 A1 | 6/2011 | Nakano | |
| 2012/0063660 A1 | 3/2012 | Imamura et al. | |
| 2015/0092160 A1 * | 4/2015 | Chen | A61B 3/0025 351/206 |
| 2015/0244941 A1 * | 8/2015 | Nishimori | H04N 5/23212 348/240.2 |

FOREIGN PATENT DOCUMENTS

| | | |
|---|---|---|
| CN | 101803364 A | 8/2010 |
| CN | 102397055 A | 4/2012 |
| CN | 103211574 A | 7/2013 |
| EP | 2422690 A1 | 2/2012 |
| JP | 2009-010890 A | 1/2009 |
| JP | 2011-194060 A | 10/2011 |
| JP | 2015-91552 A | 5/2015 |
| WO | 2011/114686 A1 | 9/2011 |

* cited by examiner

Primary Examiner — Mohammed Hasan
(74) Attorney, Agent, or Firm — Canon USA Inc., IP Division (57) ABSTRACT

An image processing apparatus converts an intensity distribution of at least one of a plurality of regions of a tomographic image of an eye by using an amount of conversion which is greater than an amount of conversion used to convert an intensity distribution of another one of the plurality of regions, the tomographic image being obtained by performing tomographic imaging on the eye by using optical interference.

19 Claims, 9 Drawing Sheets

IMAGE PROCESSING APPARATUS, IMAGE PROCESSING METHOD, AND OPTICAL COHERENCE TOMOGRAPHY APPARATUS

BACKGROUND OF THE INVENTION

Field of the Invention

The present invention relates to an image processing apparatus and an image processing method for processing a tomographic image obtained by performing tomographic imaging of an eye by using optical interference. The present invention also relates to an optical coherence tomography apparatus that performs tomographic imaging of an eye by using optical interference.

Description of the Related Art

Optical coherence tomography (OCT) apparatuses that utilize multiple-wavelength optical interference are being applied to human organisms in various fields. For example, the optical coherence tomography apparatuses are used to obtain information about internal organs with an endoscope or to obtain information about retinas with an ophthalmologic apparatus. In outpatient clinics that specialize in retinal care, an optical coherence tomography apparatus applicable to eyes is becoming an indispensable ophthalmologic device. Such an optical coherence tomography apparatus irradiates a sample with measuring light, which is low coherent light, and measures backscattered light from the sample by using an interference system. When the optical coherence tomography apparatus is applied to an eye to be examined, a high-resolution tomographic image of the eye can be obtained by scanning the eye with the measurement light. For this reason, optical coherence tomography apparatuses are widely used, for example, for ophthalmic diagnosis of retinas.

When obtaining a tomographic image of an eye fundus with an optical coherence tomography apparatus, it is difficult to obtain a high-quality tomographic image by scanning the eye with the measurement light once because of the problems of sensitivity and noise. Accordingly, Japanese Patent Laid-Open No. 2015-91552 discloses a technology for increasing the quality of tomographic images by scanning the same portion of an eye to be examined a plurality of times to obtain a plurality of tomographic images, positioning the tomographic images, and then determining the addition average of the tomographic images.

SUMMARY OF THE INVENTION

An image processing apparatus according to an aspect of the present invention includes a tomographic-image acquiring unit configured to acquire a tomographic image of an eye obtained by performing tomographic imaging on the eye by using optical interference; and a processing unit configured to convert an intensity distribution of at least one of a plurality of regions of the tomographic image by using an amount of conversion which is greater than an amount of conversion used to convert an intensity distribution of another one of the plurality of regions.

Further features of the present invention will become apparent from the following description of exemplary embodiments with reference to the attached drawings.

DESCRIPTION OF THE EMBODIMENTS

When generating a tomographic image, an optical coherence tomography apparatus measures the intensity of interference light by using a sensor and subjects the intensity information of the measured interference light to Fourier transformation and logarithmic transformation to obtain original data of a tomographic image. The original data of the tomographic image obtained by Fourier transformation and logarithmic transformation is generally about 32 bits of floating point data or 10 or more bits of integer data, and cannot be directly displayed on an ordinary display. Therefore, the original data of the tomographic image needs to be converted into 8-bit integer data that can be displayed on an ordinary display.

The original data of the tomographic image has a high dynamic range including very low intensity information and high intensity information. In contrast, 8-bit integer data that can be displayed on an ordinary display has a relatively low dynamic range. Therefore, when the original data having a high dynamic range is simply converted into 8-bit integer data, the contrast of a retina, which is important for diagnosis of an eye fundus, is greatly reduced. Therefore, in a general optical coherence tomography apparatus, when the original data is converted into 8-bit integer data, a certain amount of low-intensity-side data is discarded to ensure appropriate contrast of the retina.

However, when the low-intensity-side information is discarded, information of a vitreous body and a choroid included in the original data of the tomographic image will be lost and it will be difficult to observe the internal structure of the vitreous body and choroid in detail.

In recent years, there has been a need to observe the internal structure of the vitreous body in more detail. However, when the original data of the tomographic image is converted into 8-bit integer data so as to ensure appropriate contrast of the vitreous body, the contrast of the retina will be reduced, and it will be difficult to observe the internal structure of the retina in detail.

In light of the above-described circumstances, an embodiment enables detailed observation of internal structures of a plurality of regions (for example, retina and vitreous body) on a tomographic image of an eye.

An image processing apparatus according to an embodiment converts an intensity distribution of at least one of a plurality of regions of a tomographic image of an eye by using an amount of conversion greater than an amount of conversion used to convert an intensity distribution of another one of the plurality of regions, the tomographic image being obtained by performing tomographic imaging on the eye by using optical interference.

Accordingly, the internal structures of a plurality of regions (for example, retina and vitreous body) can be observed in detail on a tomographic image of an eye.

Embodiments of the present invention will now be described.

Structure of Optical Coherence Tomography Apparatus

Figure 1:
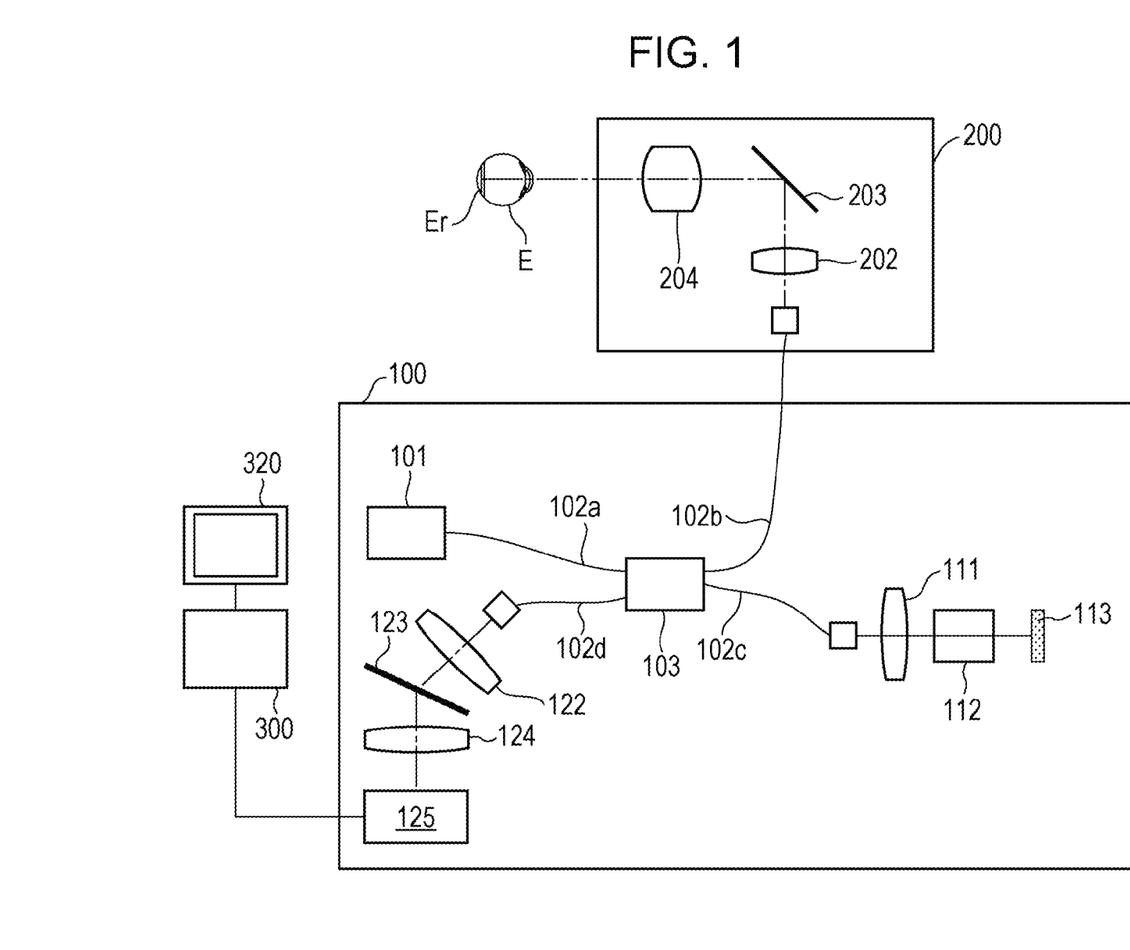
FIG. 1 illustrates an example of an optical coherence tomography apparatus according to an embodiment.

FIG. 1 illustrates an optical coherence tomography apparatus according to an embodiment. An optical interference section 100 includes a light source 101, which is a low coherent light source that emits near infrared light. Light emitted from the light source 101 propagates through an optical fiber 102a, and is divided into measurement light and reference light by a light dividing unit 103. The measurement light emitted from the light dividing unit 103 enters an optical fiber 102b, and is guided to a scanning optical system 200. The reference light emitted from the light dividing unit 103 enters an optical fiber 102c, and is guided to a reflection mirror 113. The reference light that has entered the optical fiber 102c is emitted from an end of the optical fiber 102c, passes through a collimating optical system 111 and a dispersion compensation optical system 112, and is guided to the reflection mirror 113. The reference light is reflected by the reflection mirror 113, travels along the reverse optical path, and enters the optical fiber 102c again. The dispersion compensation optical system 112 compensates for the dispersion of the scanning optical system 200 and the optical system of the eye E to be examined, which is a measurement target. The reflection mirror 113 can be driven in an optical axis direction by an optical-path-length controller (not shown), so that the optical path length of the reference light can be changed relative to the optical path length of the measurement light. The measurement light that has entered the optical fiber 102b is emitted from an end of the optical fiber 102b. The light source 101 and the optical-path-length controller are controlled by a control unit (not shown).

The light source 101 is, for example, a super luminescent diode (SLD), which is a typical low coherent light source, and has a central wavelength of 855 nm and a wavelength bandwidth of about 100 nm. The wavelength bandwidth affects the longitudinal resolution, which is the resolution in the optical axis direction, of the tomographic image, and is therefore an important parameter. Although an SLD is selected as the light source, the type of the light source is not limited as long as low coherent light can be emitted. For example, amplified spontaneous emission (ASE) may instead be used. Near infrared light is suitable for use in the measurement of an eye, and accordingly the central wavelength is set to 855 nm in the present embodiment. For the purpose of diagnosis, it is desirable to enable clear observation of membranes thinner than the junction between photoreceptor inner and outer segments (IS/OS) and the external limiting membrane (ELM). To achieve this, the longitudinal resolution of the OCT image needs to be 5 μm or less, more preferably, 3 μm or less. The longitudinal resolution depends on the wavelength bandwidth of the OCT light source. To achieve the longitudinal resolution of 3 μm or less, the wavelength bandwidth of the OCT light source needs to be about 100 nm or more.

The scanning optical system 200 will now be described. The scanning optical system 200 is configured to be movable relative to the eye E to be examined. The scanning optical system 200 is provided with a drive controller (not shown) that is capable of driving the scanning optical system 200 in the up-down and left-right directions relative to the eye axis of the eye E to be examined. The light emitted from the end of the optical fiber 102b is substantially collimated by an optical system 202, and is incident on a scanning unit 203. The scanning unit 203 includes two galvano-mirrors having rotatable mirror surfaces. One galvano-mirror deflects light in a horizontal direction, and the other galvano-mirror deflects light in a vertical direction. Thus, the scanning unit 203 deflects the incident light under the control of the drive controller (not shown). In this manner, the scanning unit 203 scans light in two directions, which are a main scanning direction along the plane of FIG. 1 and a sub-scanning direction perpendicular to the plane of FIG. 1. The light scanned by the scanning unit 203 passes through a lens 204 and forms an illumination spot on the eye E to be examined. The illumination spot moves along the eye E to be examined in response to the in-plane deflection by the scanning unit 203. The light reflected by the eye E to be examined at the illumination spot travels along the reverse optical path, enters the optical fiber 102b, and returns to the light dividing unit 103.

Figure 2:
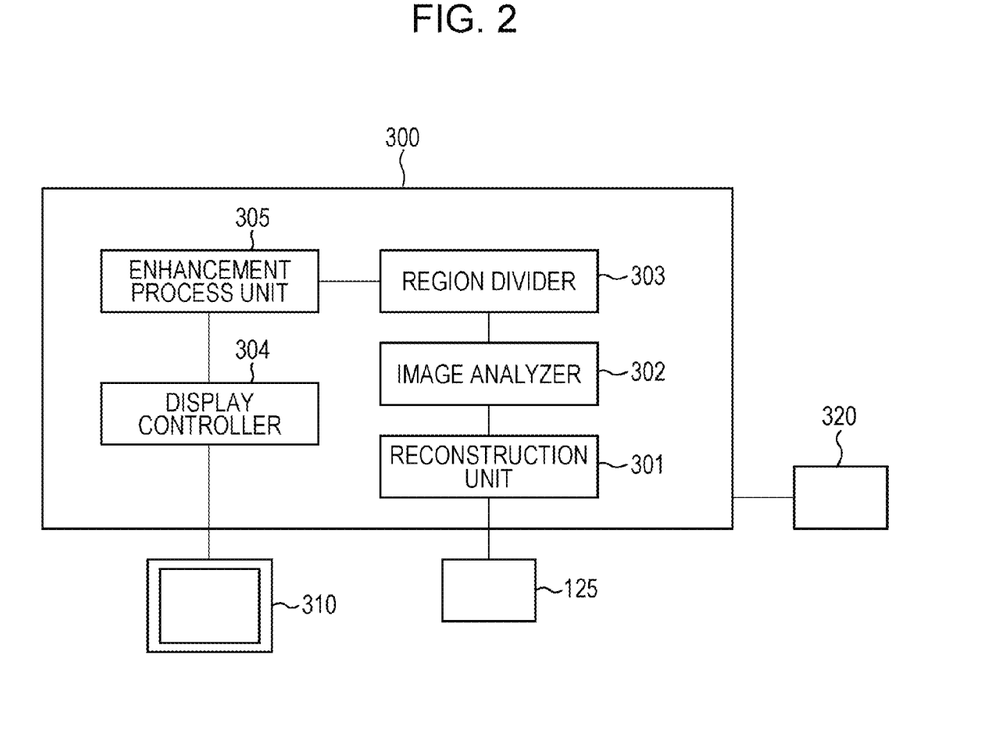
FIG. 2 illustrates an example of an image processing apparatus according to the embodiment.

As described above, the reference light reflected by the reflection mirror 113 and the measurement light reflected by the eye E to be examined return to the light dividing unit 103 as returning light, and interfere with each other so that interference light is generated. The interference light passes through an optical fiber 102d and is emitted toward a lens 122. Then, the interference light is substantially collimated and enters a diffraction grating 123. The diffraction grating 123 has a periodic structure, and divides the interference light incident thereon into interference light components. The interference light components are focused on a line sensor 125 by an imaging lens 124 capable of changing the focusing state. The line sensor 125 is connected to an image processing apparatus 300. Structure of Image Processing Apparatus FIG. 2 illustrates the image processing apparatus 300. Referring to FIG. 2, the image processing apparatus 300 includes a reconstruction unit 301 that generates original data of a tomographic image. The optical coherence tomography apparatus of the present embodiment is a Fourier-domain optical coherence tomography apparatus that generates original data of a tomographic image of an eye to be examined by subjecting data output by the line sensor 125 to wave number conversion, Fourier transformation, and logarithmic transformation performed by the reconstruction unit 301. Although a Fourier-domain optical coherence tomography apparatus is used in the present embodiment, a time-domain optical coherence tomography apparatus may instead be used. The reconstruction unit 301 is an example of a tomographic-image acquiring unit according to the present embodiment. The reconstruction unit 301 may acquire a tomographic image by receiving an interference signal generated when the line sensor 125 detects the interference light and reconstructing the tomographic image by using the received interference signal. Alternatively, the reconstruction unit 301 may acquire a tomographic image by receiving tomographic image data generated by the optical coherence tomography apparatus.

The image processing apparatus 300 also includes an image analyzer 302 that analyzes the generated original data of the tomographic image. The image analyzer 302 is capable of analyzing the original data of the tomographic image of the eye to be examined to analyze the structures of the eye to be examined included in the original data of the tomographic image. A region divider 303 is a processor for dividing the original data of the tomographic image of the eye to be examined into a plurality of regions. An enhancement process unit 305 performs contrast and intensity adjustment on the divided regions of the original data of the tomographic image. The enhancement process unit 305 is connected to a display 310, which serves as a display unit, so that the tomographic image that has been subjected to the enhancement process can be displayed. The image processing apparatus 300 is connected to a pointing device 320. The pointing device 320 is, for example, a mouse including a rotating wheel and a button, and is capable of specifying any position on the display unit 301. In the present embodiment, a mouse is used as the pointing device. However, other pointing devices such as a joystick, a touch pad, a trackball, a touch panel, and a stylus pen may instead be used.

Thus, the optical coherence tomography apparatus includes the optical interference section 100, the scanning optical system 200, and the image processing apparatus 300. At least one or more of the hardware components of the image processing apparatus 300 may be formed as an independent device. Alternatively, the components may be provided as software that can be installed in one or more computers and that realizes the corresponding functions when executed by CPUs (not shown) of the computers. In the present embodiment, it is assumed that the components are realized as software installed in a single computer.

The CPU controls the overall operation of the computer by using programs and data stored in a RAM (not shown) and a ROM (not shown). The function of each component is realized by controlling the execution of software for each component. The RAM includes an area that temporarily stores programs and data loaded from a memory medium drive, and a work area needed to enable the CPU to perform various processes. The ROM generally stores programs and setting data for the computer. The image processing apparatus 300 may instead be formed as an electric circuit composed of an image processing board. The optical coherence tomography apparatus and the image processing apparatus 300 may be formed as separate apparatuses that are linked with each other so as to enable wired or wireless communications therebetween. Alternatively, the image processing apparatus 300 may be disposed in and integrated with the optical coherence tomography apparatus.

Method for Controlling Optical Coherence Tomography Apparatus

A control method for obtaining a tomographic image of an eye to be examined by using the optical coherence tomography apparatus according to the present embodiment will now be determined. First, an operator requests a subject to sit in front of the optical coherence tomography apparatus according to the present embodiment and starts an OCT process. Light emitted from the light source 101 passes through the optical fiber 102a and is divided by the light dividing unit 103 into measurement light that travels toward the eye to be examined and reference light that travels toward the reflection mirror 113. The measurement light that travels toward the eye to be examined passes through the optical fiber 102b, and is emitted from the end of the optical fiber 102b. Then, the measurement light is substantially collimated by the optical system 202, and is incident on the scanning unit 203. The scanning unit 203 includes galvano-mirrors. The measurement light is deflected by the mirrors, passes through the lens 204, and illuminates the eye to be examined. The light is reflected by the eye to be examined, travels along the reverse optical path, and returns to the light dividing unit 103. The reference light that travels toward the reflection mirror 113 passes through the optical fiber 102c, and is emitted from the end of the optical fiber 102c. The reference light passes through the collimating optical system 111 and the dispersion compensation optical system 112, and reaches the reflection mirror 113. The reference light is reflected by the reflection mirror 113, travels along the reverse optical path, and returns to the light dividing unit 103. The measurement light and the reference light that have returned to the light dividing unit 103 interfere with each other so that interference light is generated. The interference light enters the optical fiber 102d, is substantially collimated by the lens 122, and is incident on the diffraction grating 123. The interference light that has entered the diffraction grating 123 is focused on the line sensor 125 by the imaging lens 124, so that an interference signal for a single point on the eye to be examined can be obtained.

The interference signal acquired by the line sensor 125 is output to the image processing apparatus 300. The interference signal output by the line sensor 125 is 12-bit integer data. The reconstruction unit 301 subjects the 12-bit integer data to wave number conversion, fast Fourier transformation (FFT), and logarithmic transformation, thereby generating original data of a tomographic image in the depth direction at a single point of the eye to be examined. The original data of the tomographic image generated by the reconstruction unit 301 is 32-bit floating-point data. In general, when the interference signal is subjected to FFT, floating point data including decimal numbers is generated. Therefore, when the interference signal is subjected to FFT, the generated data has a larger number of bits than the 12-bit integer data. The number of bits of the data obtained by subjecting the interference signal to FFT is not necessarily 32 as long as it is greater than the number of bits of the interference signal, and may be, for example, 16 or 64.

After the interference signal for a single point on the eye to be examined is acquired, the scanning unit 203 drives the galvano-mirrors so that interference light for another point on the eye to be examined is generated. The interference light for the other point reaches the line sensor 125, and the reconstruction unit 301 generates original data of a tomographic image in the depth direction at the other point of the eye to be examined. This control process is repeated to obtain original data of a single tomographic image of the eye to be examined. Here, two operation modes are provided: a first mode in which a certain location of the eye to be examined is scanned a plurality of times to acquire original data of a tomographic image, and a second mode in which a certain location of the eye to be examined is scanned a plurality of times to acquire original data of a plurality of tomographic images.

In the first mode, the reconstruction unit 301 generates original data of a single tomographic image. In the second mode, the reconstruction unit 301 performs positioning of original data of the tomographic images that have been acquired, and superposes (determines the average of) the original data of the tomographic images to generate original data of a single tomographic image.

A procedure for converting an intensity distribution of at least one of a plurality of regions of a tomographic image of an eye fundus by using an amount of conversion greater than that used to convert an intensity distribution of another one of the plurality of regions will now be described.

Figure 3:
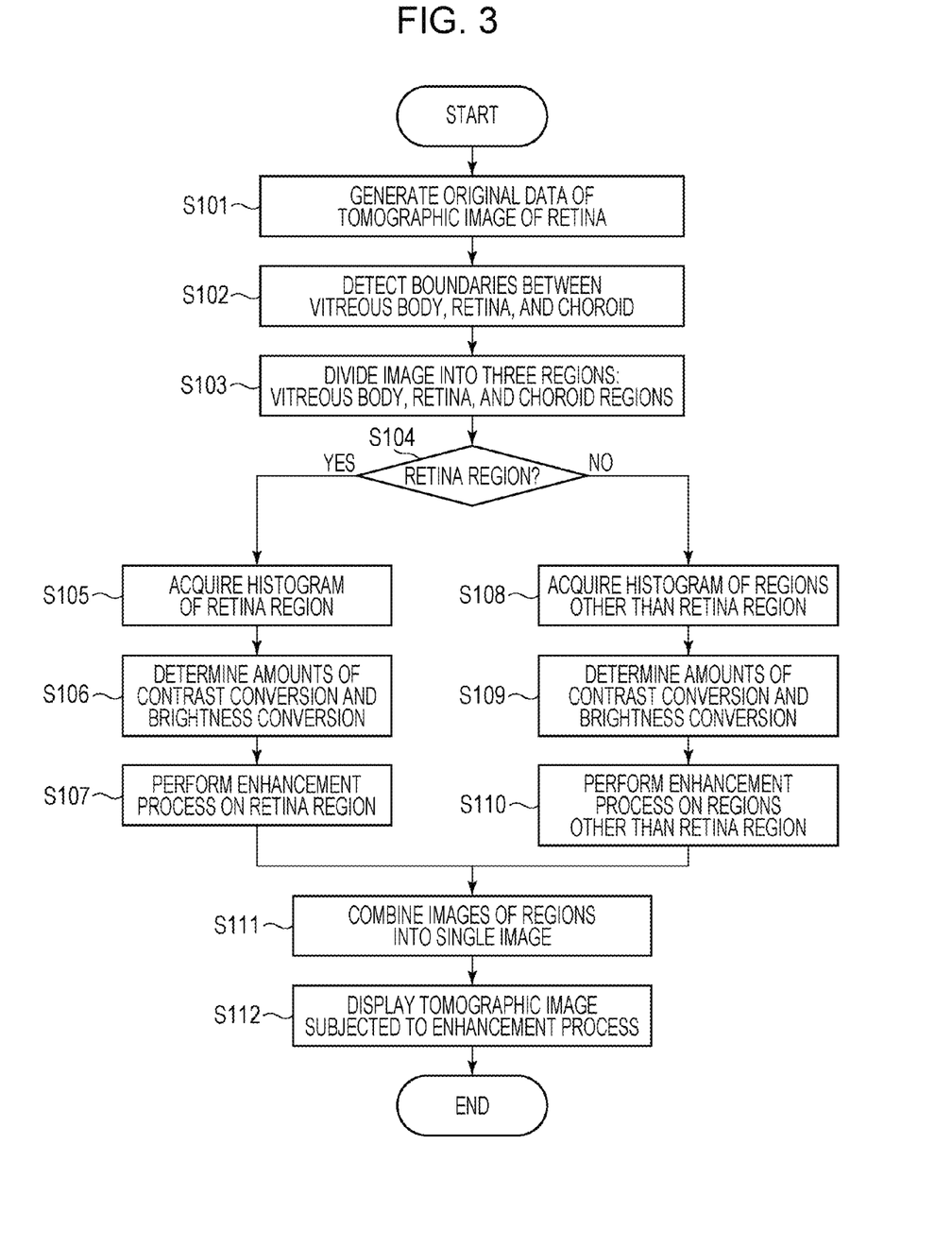
FIG. 3 is a flowchart of an example of an operation of performing an enhancement process after dividing a tomographic image of an eye fundus into a plurality of regions according to the embodiment.

A procedure for dividing a tomographic image of an eye fundus into a plurality of regions and performing intensity and contrast adjustment on each of the regions in the optical coherence tomography apparatus according to the present embodiment will now be described with reference to FIG. 3. FIG. 3 is a flowchart of an example of an operation of performing an enhancement process after dividing a tomographic image of an eye fundus into a plurality of regions according to the present embodiment.

Figure 4:
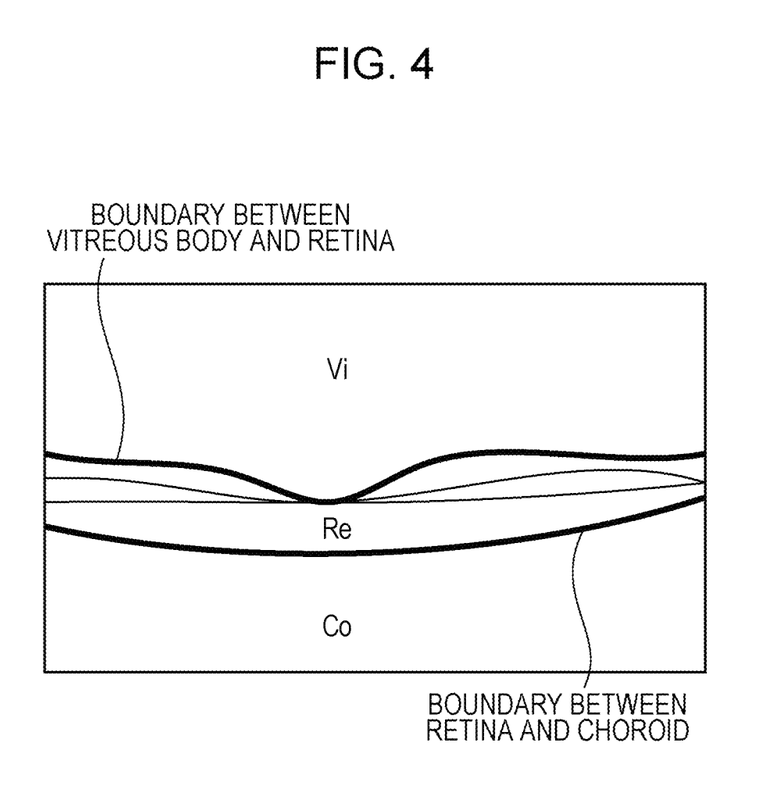
FIG. 4 illustrates the boundaries between a retina, a vitreous body, and a choroid according to the embodiment.

First, in step S101, the reconstruction unit 301 generates original data of a tomographic image of a retina and outputs the generated original data of the tomographic image to the image analyzer 302. The image analyzer 302 analyzes the original data of the tomographic image and detects boundaries between a vitreous body and the retina and between the retina and a choroid on the tomographic image, as illustrated in FIG. 4 (step S102). The detected boundary information is output to the region divider 303, and the region divider 303 divides the tomographic image into three regions, which are a vitreous body region Vi, a retina region Re, and a choroid region Co, based on the boundary information (step S103).

The region divider 303 determines whether each of the three regions divided from each other is the retina region or a region other than the retina region (step S104). Here, it is determined that the retina region Re is the retina region and that the vitreous body region Vi and the choroid region Co are regions other than the retina region. The region determined to be the retina region by the region divider 303 is subjected to the process flow starting at step S105. The regions determined as regions other than the retina region by the region divider 303 are subjected to the process flow starting at step S108.

Figure 5A:
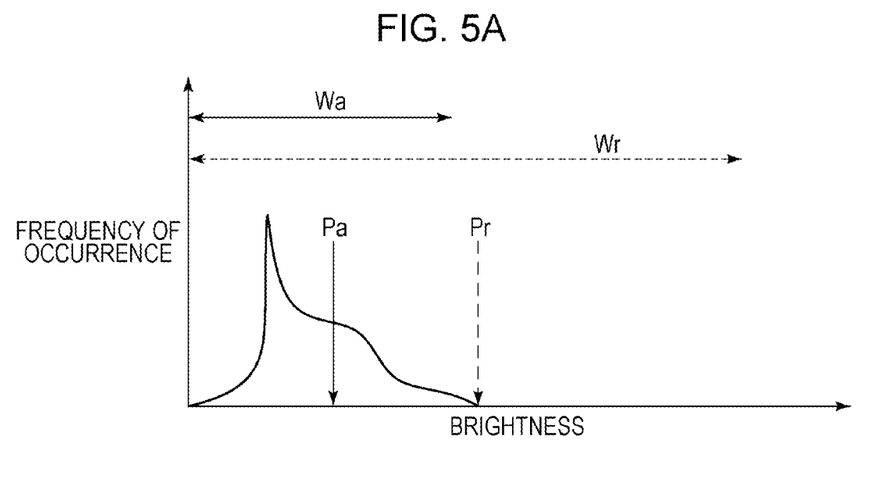
FIGS. 5A and 5B show examples of histograms of the retina region and the vitreous body and choroid regions, respectively, according to the embodiment.
Figure 6A:
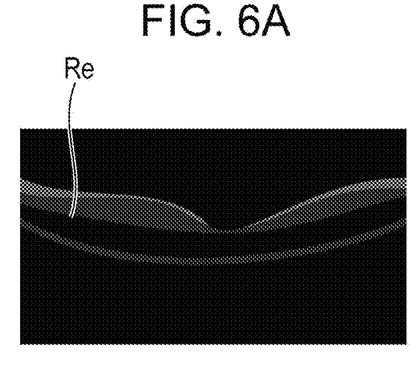
FIGS. 6A to 6E illustrate examples of enhancement processes for the retina region and the vitreous body and choroid regions, and a tomographic image of a retina after an enhancement process according to the embodiment.

In step S105, the enhancement process unit 305 acquires a histogram of the retina region Re in the original data of the tomographic image. As illustrated in FIG. 5A, the acquired histogram of the retina region Re has a small width Wa, and the brightness at the center position Pa is low. The original data of the tomographic image is 32-bit floating point data. When this data is converted into 8-bit integer data that can be displayed by the display 310 without changing the shape of the histogram, an image in which the contrast of the retina region Re is very low will be obtained, as illustrated in FIG. 6A. To avoid this, the enhancement process unit 305 sets an amount of contrast conversion Ec and an amount of intensity conversion Eb so that the width Wa of the histogram is converted into a desired width Wr and the center position Pa of the histogram is converted into a desired position Pr (step S106).

$$Ec = \frac{Wr}{Wa} \quad (1)$$

$$Eb = Pr - Pa \quad (2)$$

In step S107, the enhancement process unit 305 subjects the retina region Re, which has been determined as the retina region by the region divider 303, to an enhancement process for the original intensity Ir represented by Equation (3).

$$Ie = Ir \times Ec + Eb \quad (3)$$

Figure 6B:
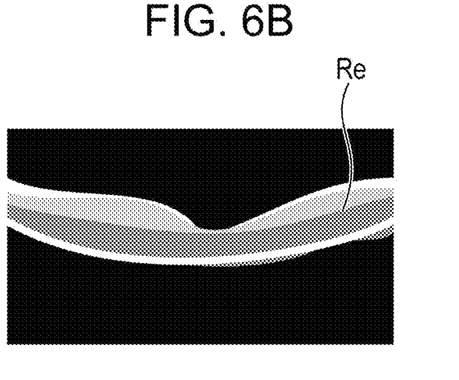

Here, Ie represents the intensity after the enhancement process, and is 8-bit integer data. As a result of this process, as illustrated in FIG. 6B, a tomographic image in which the contrast of the retina region Re is high is obtained. Therefore, the internal structure of the retina can be observed in detail. The enhancement process performed on the 32-bit data may be such that the conversion of the intensity distribution, which includes the contrast conversion, and the conversion into 8-bit data are performed simultaneously, as described above. However, the enhancement process for the 32-bit data is not limited to this, and may instead be such that the conversion of the intensity distribution is performed first, and then the conversion into 8-bit data is performed.

Figure 5B:
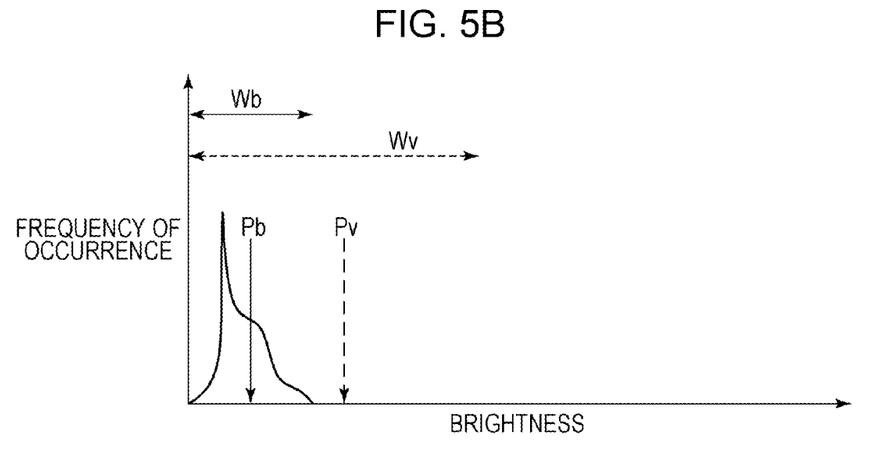
Figure 6C:
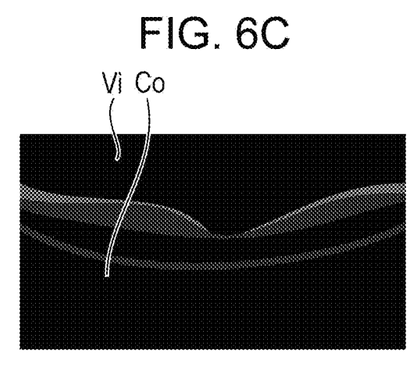

In step S108, the enhancement process unit 305 acquires a histogram of regions other than the retina region in the original data of the tomographic image. As illustrated in FIG. 5B, the acquired histogram of the regions other than the retina region has a width Wb smaller than that of the histogram of the retina region, and the brightness at the center position Pb is lower than that in the histogram of the retina region. When this data is converted into 8-bit integer data that can be displayed by the display 310 without changing the shape of the histogram, the vitreous body region Vi and the choroid region Co will be shown as nearly black images, as illustrated in FIG. 6C. To avoid this, the enhancement process unit 305 sets the amount of contrast conversion Ec and the amount of intensity conversion Eb so that the width Wb of the histogram is converted into a desired width Wv and the center position Pb of the histogram is converted into a desired position Pv (step S109). As illustrated in FIG. 5B, the intensity is lower in the vitreous body and choroid regions than in the retina region. Therefore, the amount of contrast conversion Ec and the amount of intensity conversion Eb for the regions other than the retina region are generally greater than those for the retina region.

$$Ec = \frac{Wv}{Wb} \quad (4)$$

$$Eb = Pv - Pb \quad (5)$$

In step S110, the enhancement process unit 305 subjects the vitreous body region Vi and the choroid region Co, which have been determined as the regions other than the retina region by the region divider 303, to an enhancement process for the original intensity Iv represented by Equation (6).

$$Ie = Iv \times Ec + Eb \quad (6)$$

Figure 6D:
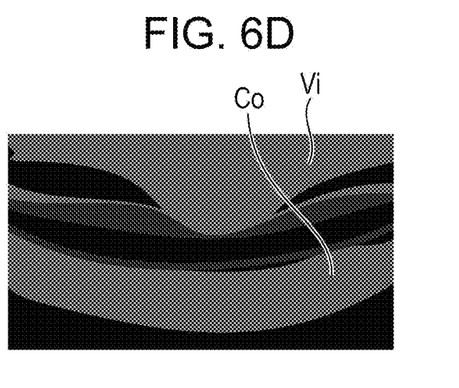

Here, Ie represents the intensity after the enhancement process, and is 8-bit integer data. As a result of this process, as illustrated in FIG. 6D, a tomographic image in which the contrasts of the vitreous body region Vi and the choroid region Co are high is obtained. Therefore, the internal structures of the vitreous body and the choroid can be observed in detail. The enhancement process performed on the 32-bit data may be such that the conversion of the intensity distribution, which includes the contrast conversion, and the conversion into 8-bit data are performed simultaneously, as described above. However, the enhancement process for the 32-bit data is not limited to this, and may instead be such that the conversion of the intensity distribution is performed first, and then the conversion into 8-bit data is performed.

Figure 6E:
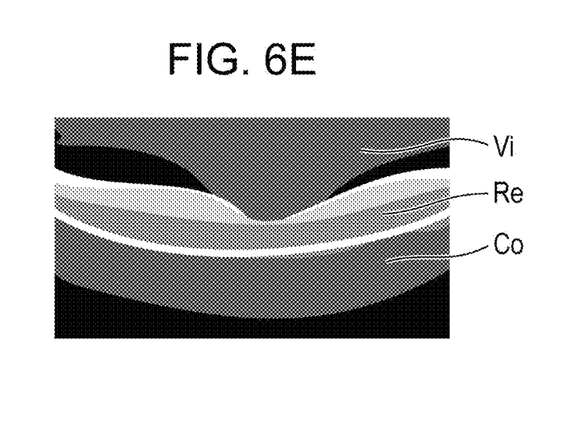

In step S111, the enhancement process unit 305 combines the image of the retina region Re subjected to the enhancement process in step S107 and the image of the vitreous body region Vi and the choroid region Co subjected to the enhancement process in step S110 to generate a single 8-bit integer format tomographic image. As illustrated in FIG. 6E, the contrast of the tomographic image generated in step S111 is high not only in the retina region Re but also in the vitreous body region Vi and the choroid region Co, so that the internal structures of the retina, the vitreous body, and the choroid can be observed in detail. The enhancement process unit 305 outputs the generated tomographic image to a display controller 304, and the display controller 304 displays the tomographic image subjected to the enhancement process on the display 310 (step S112).

In this example, the image analyzer 302 detects the boundaries between the retina, the vitreous body, and the choroid in the original data of the tomographic image. However, the regions may be subjected to different enhancement processes without performing the detection. For example, the region divider 303 may divide the original data of the tomographic image into a plurality of regions, and determine whether or not each region includes any of the retina, vitreous body, or choroid. Based on the result of the determination, it is determined whether or not each region is the retina region or a region other than the retina region. Accordingly, the regions may be subjected to different enhancement processes.

In the present embodiment, the enhancement processes are performed by dividing the original data of the tomographic image into two groups: the retina region and regions other than the retina region. However, the three regions, which are the retina region, the vitreous body region, and the choroid region, may instead be individually subjected to different enhancement processes. Furthermore, a particularly bright pigment epithelium region or a particularly dark sclera region on the retina may be specified, and the specified regions may be subjected to different enhancement processes. Although the original intensity is subjected to linear conversion in the enhancement processes of the present embodiment, the enhancement processes are not limited to linear conversion. For example, the original intensity may be converted by using a conversion function having any curve, such as a gamma curve or an S-curve.

In the present embodiment, a histogram of the retina region and a histogram the regions other than the retina region are individually acquired, and the amount of contrast conversion and the amount of intensity conversion are determined based on each histogram. However, alternatively, a single histogram may be acquired from the original data of the tomographic image, and the amount of contrast conversion and the amount of intensity conversion for each region may be determined based on the single histogram. For example, a histogram of the entire region of the image is acquired, and the amount of contrast conversion and the amount of intensity conversion for the retina region are determined based on the acquired histogram. Next, the amount of contrast conversion and the amount of intensity conversion for the retina region are increased by using a certain equation, and the increased amounts of conversion are applied to the regions other than the retina region. In such a case, it is only necessary to perform histogram calculation once.

There is no particular limitation regarding the enhancement process unit 305 as long as an intensity distribution of at least one of a plurality of regions is converted by using an amount of conversion greater than an amount of conversion used to convert an intensity distribution of another one of the regions. The enhancement process unit 305 may be configured to convert the intensity distribution of the region including at least the vitreous body, which has a relatively low intensity distribution, so that the region including at least the vitreous body is subjected to an enhancement process. The enhancement process may be any process as long as the intensity distribution of the region is converted. For example, the enhancement process unit 305 may perform only the contrast conversion among the above-described contrast conversion and intensity conversion. The enhancement process may include gradation conversion of the region instead of the contrast conversion, and the enhancement process unit 305 may convert the intensity distribution so that the slope of the gradation conversion characteristic (for example, gamma), differs between the regions. As described above, the amounts of conversion, such as the amount by which the intensity distribution is expanded and the slope of the gradation conversion characteristic, for the region including at least the vitreous body, which has a relatively low intensity distribution, may be greater than those for the other regions. Accordingly, the internal structures of the regions having different intensity distributions (for example, the retina and the vitreous body) can be observed in detail.

In the present embodiment, the retina region and the regions other than the retina region are subjected to different enhancement processes. Therefore, there is a possibility that a sudden intensity change occurs at the boundaries between the retina region and the regions other than the retina region. Such a sudden intensity change is not desirable when observing the internal structure of the eye in detail. Therefore, when the retina region and the regions other than the retina region are subjected to different enhancement processes, the enhancement processes may be performed such that the amount of contrast conversion and the amount of intensity conversion gradually change in the regions around the boundaries.

Figure 7A:
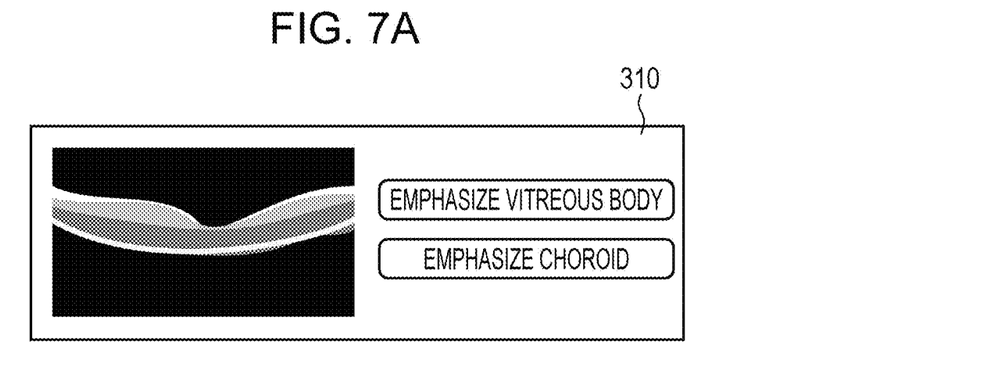
FIGS. 7A to 7C illustrate an example of a method for performing an enhancement process for a specified region based on an operator's instruction according to the embodiment.
Figure 7B:
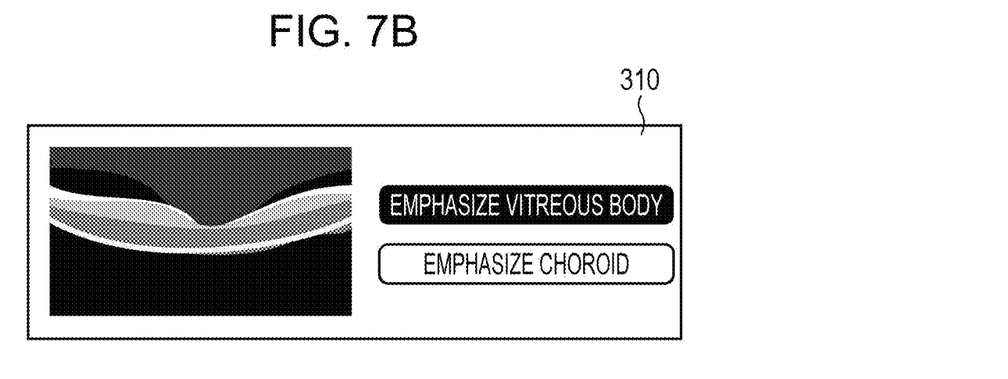
Figure 7C:
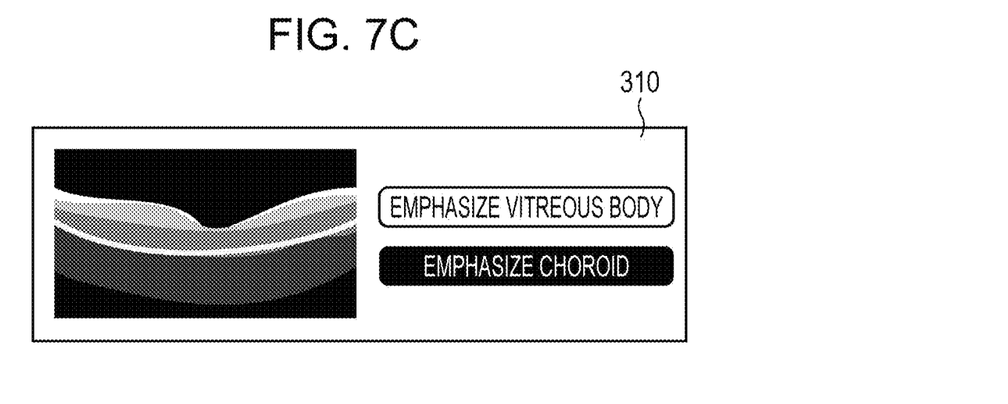

In the present embodiment, the enhancement process unit 305 subjects the retina region and the regions other than the retina region to different enhancement processes. However, the enhancement process unit 305 may perform the same enhancement process for all of the regions. For example, as illustrated in FIG. 7A, the display 310 may include a vitreous-body emphasizing button for performing an enhancement process for the vitreous body region and a choroid emphasizing button for performing an enhancement process for the choroid region. When these buttons are not pressed, the entire region of the tomographic image is subjected to the same enhancement process, and the display controller 304 displays the image after the enhancement process on the display 310. When the vitreous-body emphasizing button is pressed, as illustrated in FIG. 7B, an enhancement process for strongly emphasizing the vitreous body region is performed, and the display controller 304 displays the image after the enhancement process on the display 310. When the choroid emphasizing button is pressed, as illustrated in FIG. 7C, an enhancement process for strongly emphasizing the choroid region is performed, and the display controller 304 displays the image after the enhancement process on the display 310. The above-described process allows physicians to see an image in which the desired region is emphasized only when necessary and observe the internal structure of the desired portion.

A procedure for converting an intensity distribution of at least one of a plurality of regions of a tomographic image of an anterior eye portion by using an amount of conversion greater than that used to convert an intensity distribution of another one of the plurality of regions will now be described.

Figure 8:
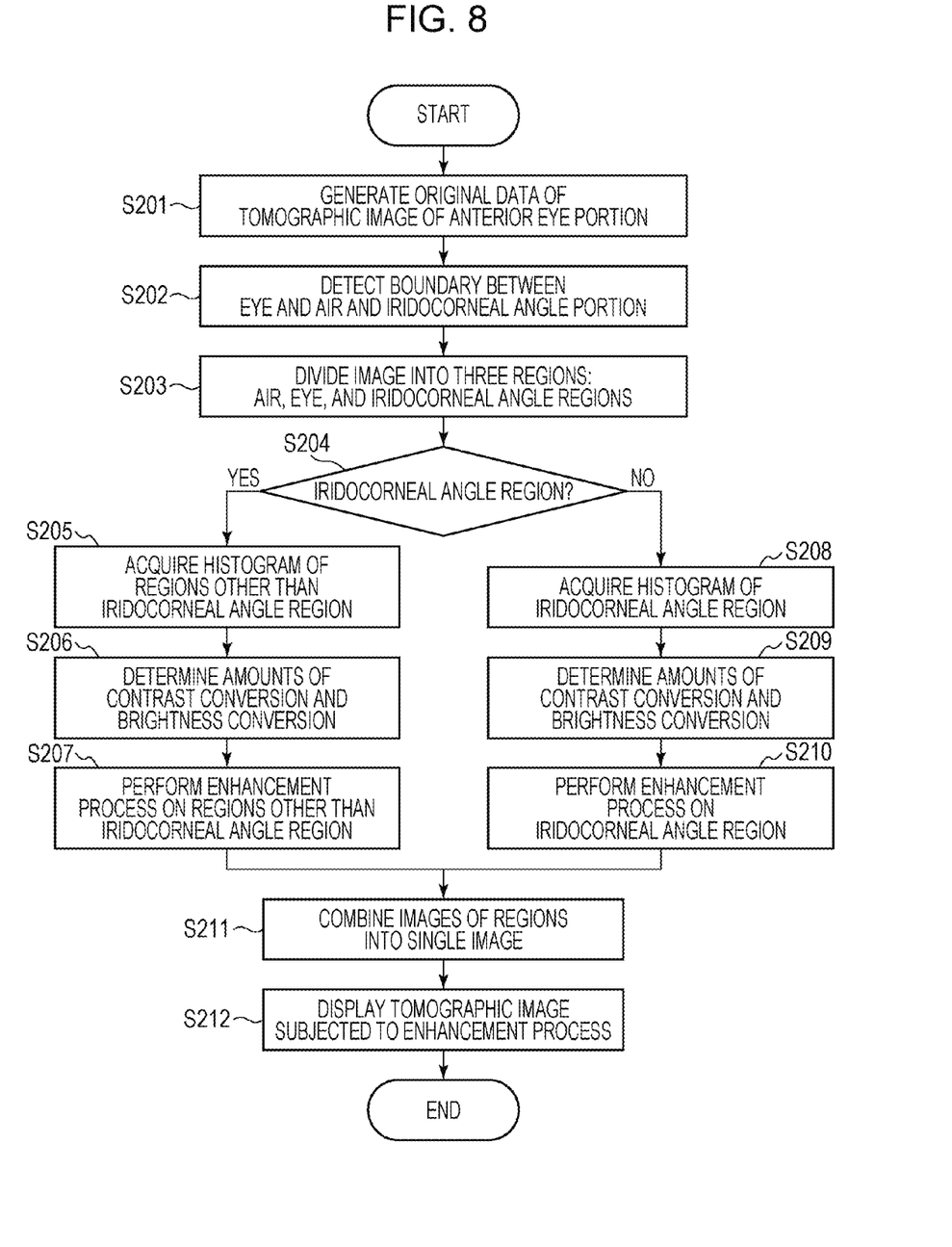
FIG. 8 is a flowchart of an example of an operation of performing an enhancement process after dividing a tomographic image of an anterior eye portion into a plurality of regions according to the embodiment.

A procedure for dividing a tomographic image of an anterior eye portion into a plurality of regions and performing intensity and contrast adjustment on each of the regions in the optical coherence tomography apparatus according to the present embodiment will now be described with reference to FIG. 8. FIG. 8 is a flowchart of an example of an operation of performing an enhancement process after dividing a tomographic image of an anterior eye portion into a plurality of regions according to the present embodiment.

First, in step S201, the reconstruction unit 301 generates original data of a tomographic image of an anterior eye portion and outputs the generated original data of the tomographic image to the image analyzer 302. The image analyzer 302 analyzes the original data of the tomographic image and detects the boundary between the air and a cornea surface and an iridocorneal angle portion on the tomographic image (step S202). The detected information is output to the region divider 303, and the region divider 303 divides the tomographic image into three regions, which are an air region Ai, an eye region Ey, and an iridocorneal angle region An, based on the detected information (step S203). The region divider 303 determines whether each of the three regions divided from each other is the iridocorneal angle region or a region other than the iridocorneal angle region (step S204). Here, it is determined that the iridocorneal angle region An is the iridocorneal angle region and that the air region Ai and the eye region Ey excluding the iridocorneal angle region are regions other than the iridocorneal angle region. The region determined to be the iridocorneal angle region by the region divider 303 is subjected to the process flow starting at step S205. The regions determined as regions other than the iridocorneal angle region by the region divider 303 are subjected to the process flow starting at step S208.

In step S205, the enhancement process unit 305 acquires a histogram of the regions other than the iridocorneal angle region in the original data of the tomographic image. The acquired histogram of the regions other than the iridocorneal angle region has a small width Wa, and the brightness at the center position Pa is low. The original data of the tomographic image is 32-bit floating point data. When this data is converted into 8-bit integer data that can be displayed by the display 310 without changing the shape of the histogram, an image in which the contrast of the eye region Ey excluding the iridocorneal angle region is very low will be obtained. To avoid this, the enhancement process unit 305 sets an amount of contrast conversion Ec and an amount of intensity conversion Eb so that the width Wa of the histogram is converted into a desired width Wc and the center position Pa of the histogram is converted into a desired position Pc (step S206).

$$Ec = \frac{Wc}{Wa} \quad (7)$$

$$Eb = Pc - Pa \quad (8)$$

In step S207, the enhancement process unit 305 subjects the regions that have been determined as the regions other than the iridocorneal angle region by the region divider 303 to an enhancement process for the original intensity Ic represented by Equation (9).

$$Ie = Ic \times Ec + Eb \quad (9)$$

Here, Ie represents the intensity after the enhancement process, and is 8-bit integer data. As a result of this process, a tomographic image in which the contrast of the eye region Ey excluding the iridocorneal angle region is high is obtained. Therefore, the internal structure of, for example, the cornea can be observed in detail.

In step S208, the enhancement process unit 305 acquires a histogram of the iridocorneal angle region in the original data of the tomographic image. The acquired histogram of the iridocorneal angle region has a width Wb smaller than that of the histogram of the regions other than the iridocorneal angle region, and the brightness at the center position Pb is lower than that in the histogram of the regions other than the iridocorneal angle region. When this data is converted into 8-bit integer data that can be displayed by the display 310 without changing the shape of the histogram, the iridocorneal angle region An will be shown as a nearly black image. To avoid this, the enhancement process unit 305 sets the amount of contrast conversion Ec and the amount of intensity conversion Eb so that the width Wb of the histogram is converted into a desired width Wn and the center position Pb of the histogram is converted into a desired position Pn (step S209). The intensity is lower in the iridocorneal angle region than in the regions other than the iridocorneal angle region. Therefore, the amount of contrast conversion Ec and the amount of intensity conversion Eb for the iridocorneal angle region are generally greater than those for the regions other than the iridocorneal angle region.

$$Ec = \frac{Wn}{Wb} \quad (10)$$

$$Eb = Pn - Pb \quad (11)$$

In step S210, the enhancement process unit 305 subjects the iridocorneal angle region An, which has been determined as the iridocorneal angle region by the region divider 303, to an enhancement process for the original intensity In represented by Equation (12).

$$Ie = In \times Ec + Eb \quad (12)$$

Here, Ie represents the intensity after the enhancement process, and is 8-bit integer data. As a result of this process, a tomographic image in which the contrast of the iridocorneal angle region An is high is obtained. Therefore, the internal structure of the iridocorneal angle portion can be observed in detail. In step S211, the enhancement process unit 305 combines the image of the regions other than the iridocorneal angle region subjected to the enhancement process in step S207 and the image of the iridocorneal angle region An subjected to the enhancement process in step S210 to generate a single 8-bit integer format tomographic image. The contrast of the tomographic image generated in step S211 is high not only in the eye region Ey excluding the iridocorneal angle region An but also in the iridocorneal angle region An, so that the internal structure of the eye including the iridocorneal angle portion can be observed in detail. The enhancement process unit 305 outputs the generated tomographic image to the display controller 304, and the display controller 304 displays the tomographic image subjected to the enhancement process on the display 310 (step S212).

In this example, the image analyzer 302 detects the boundary between the air and the cornea surface and the iridocorneal angle portion in the original data of the tomographic image. However, the regions may be subjected to different enhancement processes without performing the detection. For example, the region divider 303 may divide the original data of the tomographic image into a plurality of regions, and determine whether or not each region includes any of the air, an eye portion other than the iridocorneal-angle portion, or the iridocorneal-angle portion. Based on the result of the determination, it is determined whether or not each region is the iridocorneal angle region or a region other than the iridocorneal angle region. Accordingly, the regions may be subjected to different enhancement processes.

In the present embodiment, the enhancement process is performed by dividing the original data of the tomographic image into two groups: the iridocorneal angle region and regions other than the iridocorneal angle region An. However, the three regions, which are the air region, the eye region excluding the iridocorneal angle region, and the iridocorneal angle region, may instead be individually subjected to different enhancement processes. Furthermore, a sclera, an anterior chamber, a crystalline lens, a ciliary body, or a vitreous body that can be observed in the tomographic image may be specified, and the specified regions may be subjected to different enhancement processes. In particular, although the air region outside the eye appears in the tomographic image of the anterior eye portion, the air region is not used for diagnosis. Therefore, the amount of contrast conversion and the amount of intensity conversion for the air region may be reduced. Alternatively, the enhancement process for the air region may be omitted.

As described above, the tomographic image is divided into a plurality of regions, and each region is subjected to the corresponding enhancement process. Accordingly, the contrast can be increased in each region, and the internal structures of a plurality of portions can be observed in detail.

Figure 9A:
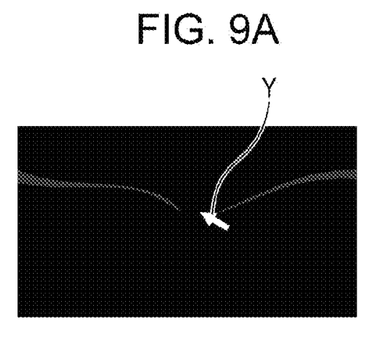
FIGS. 9A to 9E illustrate an example of a method for performing an enhancement process for a specified region based on an operation of a pointing device according to the embodiment.

A procedure for dividing an original data of a tomographic image into a plurality of regions and adjusting the intensity and contrast for a region specified on the basis of an operation of a pointing device in the optical coherence tomography apparatus will now be described. Enhancement Process of Specified Region in Retina The reconstruction unit 301 generates original data of a tomographic image of a retina and outputs the generated original data of the tomographic image to the image analyzer 302. The image analyzer 302 analyzes the received original data of the tomographic image and detects boundaries between a vitreous body and the retina and between the retina and a choroid on the tomographic image, as illustrated in FIG. 4. The detected boundary information is output to the region divider 303, and the region divider 303 divides the tomographic image into three regions, which are a vitreous body region Vi, a retina region Re, and a choroid region Co, based on the received boundary information. The enhancement process unit 305 subjects the entirety of the original data of the tomographic image to an enhancement process. The processed tomographic image is displayed on the display 310. As illustrated in FIG. 9A, the display 310 displays not only the tomographic image but also a cursor Y that indicates a position specified by a pointing device. When a dragging operation, which is an operation of moving the pointing device while pressing a button (not shown) on the pointing device, is performed while the cursor Y of the pointing device is displayed on the tomographic image, the following operation is performed.

Figure 9B:
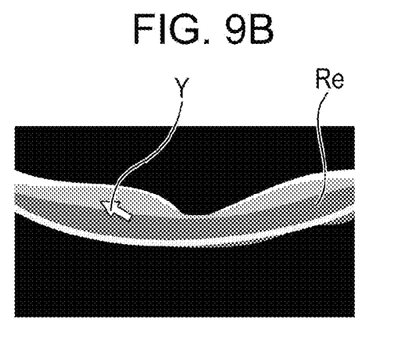
Figure 9C:
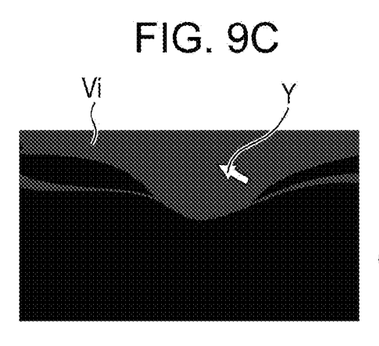
Figure 9D:
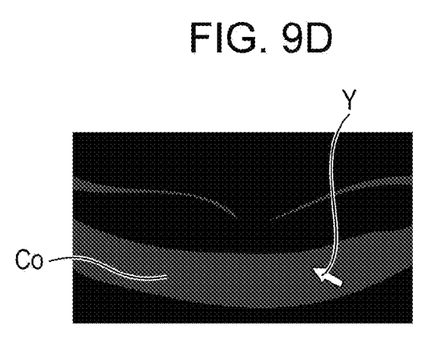

First, the region in which the cursor Y is positioned is selected from the three regions. When it is determined that the cursor Y is in the vitreous body region Vi, as illustrated in FIG. 9C, the enhancement process unit 305 performs the enhancement process on the vitreous body region Vi on the basis of the operation signal of the pointing device. When it is determined that the cursor Y is in the retina region Re, as illustrated in FIG. 9B, the enhancement process unit 305 performs the enhancement process on the retina region Re on the basis of the operation signal of the pointing device. When it is determined that the cursor Y is in the choroid region Co, as illustrated in FIG. 9D, the enhancement process unit 305 performs the enhancement process on the choroid region Co on the basis of the operation signal of the pointing device.

In the present embodiment, a mouse is used as the pointing device. However, other pointing devices such as a joystick, a touch pad, a trackball, a touch panel, and a stylus pen may instead be used. Furthermore, the enhancement process may be performed on the basis of an operation signal generated by any operation of the pointing device other than the position specifying operation, such as a wheel-rotating operation or a sliding operation, instead of the dragging operation.

Figure 9E:
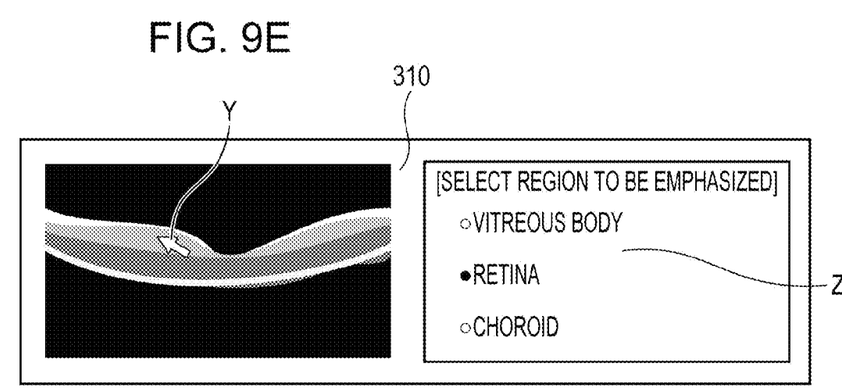

In the present embodiment, the region to be enhanced is determined on the basis of the position of the cursor Y. However, the region to be enhanced can be specified by another method. For example, as illustrated in FIG. 9E, a region selecting button Z may be displayed on the display 310, and the region to be subjected to the enhancement process may be determined on the basis of the result of selection of the region selecting button Z. Enhancement Process of Specified Region in Anterior Eye Portion First, the reconstruction unit 301 generates original data of a tomographic image of an anterior eye portion and outputs the generated original data of the tomographic image to the image analyzer 302. The image analyzer 302 analyzes the original data of the tomographic image and detects the boundary between the air and a cornea surface and an iridocorneal angle portion on the tomographic image. The detected information is output to the region divider 303, and the region divider 303 divides the tomographic image into three regions, which are an air region Ai, an eye region Ey, and an iridocorneal angle region An, based on the detected information. The enhancement process unit 305 subjects the entirety of the original data of the tomographic image to an enhancement process. The processed tomographic image is displayed on the display 310. The display 310 displays not only the tomographic image subjected to the enhancement process but also a cursor Y that indicates a position specified by a pointing device. When a dragging operation, which is an operation of moving the pointing device while pressing a button (not shown) on the pointing device, is performed while the cursor Y of the pointing device is displayed on the tomographic image, the following operation is performed.

First, the region in which the cursor Y is positioned is selected from the three regions. When it is determined that the cursor Y is in the eye region Ey, the enhancement process unit 305 performs the enhancement process on the eye region Ey on the basis of the operation signal of the pointing device. When it is determined that the cursor Y is in the iridocorneal angle region An, the enhancement process unit 305 performs the enhancement process on the iridocorneal angle region An on the basis of the operation signal of the pointing device. When it is determined that the cursor Y is in the air region Ai, the enhancement process unit 305 does not perform the enhancement process on the air region Ai. This is because no imaging target is present in the air and the air region Ai is not used for diagnosis.

As described above, by performing the enhancement process on the specified region of the tomographic image, an image in which only the desired region is emphasized can be obtained, and the internal structure of the desired portion can be observed in detail.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-140052 filed Jul. 13, 2015, which is hereby incorporated by reference herein in its entirety.

What is claimed is:

1. An image processing apparatus comprising:
a detecting unit configured to detect at least one layer boundary on a tomographic image of an eye obtained by performing tomographic imaging on the eye by using optical interference;
a determining unit configured to determine, based on the detected at least one layer boundary, a region of the tomographic image including a retina of the eye; and
a processing unit configured to convert an intensity distribution of a region other than the region including the retina by using an amount of conversion which is greater than an amount of conversion used to convert an intensity distribution of the region including the retina.

2. The image processing apparatus according to claim 1, wherein the processing unit expands the intensity distribution of the region other than the region including the retina by using an amount of conversion greater than an amount of conversion used to expand the intensity distribution of the region including the retina.

3. The image processing apparatus according to claim 1, wherein the processing unit performs a gradation conversion on the intensity distribution of the region other than the region including the retina by using a gradation conversion characteristic with a slope greater than a slope of a gradation conversion characteristic used to perform a gradation conversion on the intensity distribution of the region including the retina.

4. The image processing apparatus according to claim 1, wherein the detecting unit detects, as the at least one layer boundary, a layer boundary between the retina and a vitreous body of the tomographic image of the eye, and
wherein the determining unit determines, based on the layer boundary between the retina and the vitreous body, that a region of the tomographic image including the vitreous body is the region other than the region including the retina.

5. The image processing apparatus according to claim 1, wherein the processing unit converts an image, obtained by converting the intensity distribution of the region other than the region including the retina, into data having a number of bits that enables displaying on a display unit.

6. The image processing apparatus according to claim 1, further comprising:
an acquiring unit connectable to an optical coherence tomography apparatus, which performs tomographic imaging on the eye by using optical interference, so as to enable communications therebetween, the acquiring unit being configured to acquire the tomographic image of the eye as a result of the optical coherence tomography apparatus performing tomographic imaging on the eye.

7. An optical coherence tomography apparatus comprising:
a first detecting unit configured to detect interference light obtained by interference of returning light and reference light, the returning light returning from an eye irradiated with measurement light, the reference light corresponding to the measurement light;
a tomographic-image acquiring unit configured to acquire a tomographic image of the eye based on the detected interference light;
a second detecting unit configured to detect at least one layer boundary of the tomographic image;
a determining unit configured to determine, based on the detected at least one layer boundary, a region of the tomographic image including a retina of the eye; and
a processing unit configured to convert an intensity distribution of a region other than the region including the retina by using an amount of conversion which is greater than an amount of conversion used to convert an intensity distribution of the region including the retina.

8. The optical coherence tomography apparatus according to claim 7, wherein a longitudinal resolution of the tomographic image is 5 µm or less.

9. The optical coherence tomography apparatus according to claim 7, wherein a longitudinal resolution of the tomographic image is 3 µm or less.

10. An image processing method comprising:
detecting at least one layer boundary on a tomographic image of an eye obtained by performing tomographic imaging on the eye by using optical interference;
determining, based on the detected at least one layer boundary, a region of the tomographic image including a retina of the eye; and
converting an intensity distribution of a region other than the region including the retina by using an amount of conversion which is greater than an amount of conversion used to convert an intensity distribution of the region including the retina.

11. An image processing apparatus comprising:
a tomographic-image acquiring unit configured to acquire a tomographic image of an eye obtained by performing tomographic imaging on the eye by using optical interference; and
a processing unit configured to measure widths of intensity distributions of a plurality of regions of the tomographic image and convert the intensity distribution of one of the regions that has a narrow intensity distribution by using an amount of conversion which is greater than an amount of conversion used to convert the intensity distribution of another one of the regions that has a wide intensity distribution.

12. The image processing apparatus according to claim 11, wherein the processing unit performs a gradation conversion on the intensity distribution of the one of the regions that has a narrow intensity distribution by using a gradation conversion characteristic with a slope greater than a slope of a gradation conversion characteristic used to perform a gradation conversion on the intensity distribution of the other one of the regions that has a wide intensity distribution.

13. The image processing apparatus according to claim 11, wherein the processing unit measures a central position of the intensity distribution of at least one of the regions, and converts the central position of the intensity distribution of the at least one of the regions by using different amounts of conversion.

14. An image processing method comprising:
acquiring a tomographic image of an eye obtained by performing tomographic imaging on the eye by using optical interference; and
measuring widths of intensity distributions of a plurality of regions of the tomographic image and converting the intensity distribution of one of the regions that has a narrow intensity distribution by using an amount of conversion which is greater than an amount of conversion used to convert the intensity distribution of another one of the regions that has a wide intensity distribution.

15. An image processing apparatus comprising:
a display control unit configured to display a tomographic image of an eye on a display unit, the tomographic image being obtained by performing tomographic imaging on the eye by using optical interference;
a pointing device that specifies a position on the displayed tomographic image; and
a processing unit configured to convert, based on an operation signal of the pointing device, an intensity distribution of a region including the position specified by the pointing device on the displayed tomographic image by using an amount of conversion which is greater than an amount of conversion used to convert an intensity distribution of another region of the tomographic image.

16. The image processing apparatus according to claim 15, wherein the processing unit converts an intensity distribution of a region of a retina in the tomographic image when the operation signal is detected while the position specified by the pointing device is in the region of the retina, and converts an intensity distribution of a region of the tomographic image other than the retina when the operation signal is detected while the position specified by the pointing device is in the region other than the region of the retina.

17. The image processing apparatus according to claim 15, wherein the processing unit converts an intensity distribution of a region of an iridocorneal angle portion in the tomographic image when the operation signal is detected while the position specified by the pointing device is in the region of the iridocorneal angle portion, and converts an intensity distribution of a region of the tomographic image other than the iridocorneal angle portion when the operation signal is detected while the position specified by the pointing device is in the region other than the region of the iridocorneal angle portion.

18. A non-transistory computer readable storage medium storing a program for causing a computer to execute the image processing method according to claim 10.

19. A non-transistory computer readable storage medium storing a program for causing a computer to execute the image processing.

* * * * *